(12) United States Patent
Ryan

(10) Patent No.: US 8,053,195 B1
(45) Date of Patent: Nov. 8, 2011

(54) ISOLATED GENOMIC NUCLEIC ACID MOLECULES OBTAINABLE FROM CHROMOSOME 1P21-P13 THAT ENCODE HUMAN RHOC

(76) Inventor: James W. Ryan, Augusta, GA (US)

( * ) Notice: Subject to any disclaimer, the term of this patent is extended or adjusted under 35 U.S.C. 154(b) by 1214 days.

(21) Appl. No.: 10/683,016

(22) Filed: Oct. 10, 2003

Related U.S. Application Data

(60) Provisional application No. 60/418,034, filed on Oct. 12, 2002.

(51) Int. Cl.
- *C07H 21/02* (2006.01)
- *G01N 33/53* (2006.01)
- *C12P 21/04* (2006.01)
- *C12N 15/00* (2006.01)

(52) U.S. Cl. ............ 435/7.1; 536/23.1; 435/6; 435/41; 435/71.1; 435/320.1; 506/3; 506/9; 506/16; 424/1.11

(58) Field of Classification Search ................ None
See application file for complete search history.

(56) References Cited

U.S. PATENT DOCUMENTS

| 6,030,786 | A | * | 2/2000 | Cowsert | ...................... | 435/6 |
| 6,060,297 | A | * | 5/2000 | Hillman et al. | ............. | 435/196 |
| 2001/0044414 | A1 | * | 11/2001 | Clark et al. | ................. | 514/44 |

OTHER PUBLICATIONS

Birren et al., GenBank Accession No. AC024481; (http://www.ncbi.nlm.nih.gov/entrez/viewer.fcgi?db=nucleotide&val=8138477); Jun. 10, 2000.*
Blast Result Printout; http://www.ncbi.nlm.nih.gov/BLAST/.Downloaded Apr. 10, 2007.*
Wennerberg et al., Journal of Cell Science. vol. 118(5): 843-846. 2005.*
Ramsay. Molecular Biotechnology. vol. 1(2): 181-201. 1994.*
Chardin et al. (Coding sequence of human rho cDNAs clone 6 and clone 9, 1988, Nucleic Acids Research, vol. 16, p. 2717).*
Wishart et al. (PEPTOOLTM and GENETOOLTM: Platform-independent tools for biological sequence analysis, 2000, From: Methods in Molecular Biology, vol. 132: Bioinformatics Methods and Protocols, Humana Press, pp. 93-113).*
Watson et al. (Recombinant DNA, Second Edition, 1992, pp. 137-140).*
Morris et al., Reassignment of the human ARH9 RAS-related gene to chromosome 1p13-p21, 1993, Genomics, vol. 15, Abstract), 1 page.*
Werner, Computer-assisted analysis of transcription control regions, 2000, From: Methods in Molecular Biology, vol. 132: Bioinformatics Methods and Protocols, Humana Press, pp. 337-349.*
van Golen, et al. "Rho C GTPase, a novel transforming oncogene for human mammary epithelial cells . . . " Cancer Res. 2000, pp. 5832-5838, vol. 60.
Clark, et al. "Genomic analysis of metastasis reveals an essential role for RhoC" Nature 2000, pp. 532-535, vol. 406.
GenBank entry: Locus HUMRHOCA; Accession L25081; Version L25081.1 GI:407698, Jul. 3, 2006.
Kakikawa et al. "Promoter/repressor system of *Lactobacillus plantarum* phage ogle: characterization of the promoters pR49-pR-pL and overproduction of the Cro-like protein Cng in Excherichia col "Gene 1998, pp. 371-379, vol. 215.
Suwa, et al. "Overexpression of the RhoC gene correlates with progression of ductal adenocarcinoma of the pancreas" Brit. J. Cancer 1998, pp. 147-152, vol. 77.
Aepfelbacher et al., "Bacterial Toxins Block Endothelial Wound Repair" Arteriosclerosis, Thrombosis and Vascular biology 1997, pp. 1623-1629, vol. 17.
Marron et al., "Genetic and Physical Mapping of a Type 1 Diabetes Susceptibility Gene (IDDM12) to a 100-kb Phagemid Artificial Chromosome Clone Containing D2S72-CTLA4-D2S105 on Chromosome 2q33" Diabetes 2003, pp. 492-499, vol. 49.
Larin et al., "Advances in artificial chromosome technology" Trends in Genetics 2002, pp. 313-319. vol. 18.

* cited by examiner

*Primary Examiner* — Ardin Marschel
*Assistant Examiner* — Shannon Janssen
(74) *Attorney, Agent, or Firm* — Cheryl H. Agris

(57) ABSTRACT

The invention is directed to an isolated genomic nucleic acid molecule fragment that encodes human RhoC, vectors and hosts containing the fragment and fragments hybridizing to noncoding regions as well as antisense oligonucleotides to these fragments. The invention is further directed to methods of using these fragments to obtain human RhoC and to diagnose, treat, prevent and/or ameliorate a pathological disorder.

11 Claims, No Drawings

SEQUENCE LISTING

<160> NUMBER OF SEQ ID NOS: 2

<210> SEQ ID NO 1
<211> LENGTH: 193
<212> TYPE: PRT
<213> ORGANISM: Homo sapiens

<400> SEQUENCE: 1

```
Met Ala Ala Ile Arg Lys Lys Leu Val Ile Val Gly Asp Gly Ala Cys
1               5                   10                  15

Gly Lys Thr Cys Leu Leu Ile Val Phe Ser Lys Asp Gln Phe Pro Glu
            20                  25                  30

Val Tyr Val Pro Thr Val Phe Glu Asn Tyr Ile Ala Asp Ile Glu Val
        35                  40                  45

Asp Gly Lys Gln Val Glu Leu Ala Leu Trp Asp Thr Ala Gly Gln Glu
    50                  55                  60

Asp Tyr Asp Arg Leu Arg Pro Leu Ser Tyr Pro Asp Thr Asp Val Ile
65                  70                  75                  80

Leu Met Cys Phe Ser Ile Asp Ser Pro Asp Ser Leu Glu Asn Ile Pro
                85                  90                  95

Glu Lys Trp Thr Pro Glu Val Lys His Phe Cys Pro Asn Val Pro Ile
            100                 105                 110

Ile Leu Val Gly Asn Lys Lys Asp Leu Arg Gln Asp Glu His Thr Arg
        115                 120                 125

Arg Glu Leu Ala Lys Met Lys Gln Glu Pro Val Arg Ser Glu Glu Gly
    130                 135                 140

Arg Asp Met Ala Asn Arg Ile Ser Ala Phe Gly Tyr Leu Glu Cys Ser
145                 150                 155                 160

Ala Lys Thr Lys Glu Gly Val Arg Glu Val Phe Glu Met Ala Thr Arg
                165                 170                 175

Ala Gly Leu Gln Val Arg Lys Asn Lys Arg Arg Arg Gly Cys Pro Ile
            180                 185                 190

Leu
```

<210> SEQ ID NO 2
<211> LENGTH: 16347
<212> TYPE: DNA
<213> ORGANISM: Homo sapiens

<400> SEQUENCE: 2

```
gaattcacag ctgggatccg gaagcatttc taggcgcacc ctttgaggag taggtaggaa      60
ttggactcct ggaaattcca ggcccaggga agaaagcgaa ttgtgaggag gaacggtggt     120
ctgggtctga acggctctga gaggtcttca agtttggggg atgacgttgg gctgtacgat     180
cctaggaaca agagggtgga catctccccc caaccaacac acccgcgccg ggccctggga     240
cctcccggcg gataccctt  cccagtcccg cttcccgcga ggtcccaggt gcagcaggag      300
cgggtggccg cttggccaca ggagggcagc agcggccctt cctgacccca ccccgagcac     360
ctcttaactt tcccgacgcc ggtcctcccc taggggattg aaggctgggc agagtctgag     420
tccacccggg tcgtgctccc cccgctcgcc cggctcctcc gcagtccagg aatctccccg     480
tggctctccc cgacctggag gggtggacgc ccctggcccc cagtcccccgg cctgcggagg    540 gggccggtgg ctgcggccct gcgcggggcc ggggcgggcc gagccaaggg ccgccccccgg    600
```

```
ccgaccctcc ccctgccggg cccgccctcc ccgccgcggc gctggaggag ggcggggcgg      660
ggccctgggg tcagtctgag cctccggcac cggccgcgca gctggaggcg gcggagcgga      720
aggtaccctg ggccggggct gcgggcggtg gggcgtcttg ggaactcgtc cccaggagag      780
cactttccct tcctcgctgg cccggagatc ggggcccgtg cgaggagggg cttcggcctg      840
ggcgtggacc ccgttccctc caagcggagt cggcatccgg gctgggcggt ggtcggaccg      900
cgtcggcccc tccccgggct gcagcgaggg ggcccggacc tgccggcagg ggctctggcc      960
tcctgaggtc cgagtcggag ccccttccct tctcctccca gcttcccgga acctgccccg     1020
ccgggcgagg ggcgagggaa cttcaactca gacgccccag ccccagggt gggcggccgc      1080 agggaccta gagtgggatg gggtgggaat tcctccaggc caggagggag gtatggcggg      1140
aataggggcg ggatgtgacc attggggcct gccactgctc ggcagggtct ggacgccgcc     1200
ctggacggtt cctggagccc gcttgtgttg aggataaggg agatggggaa ggatccaact     1260
ctgtgtgtgt gtgtgtgtgt gtgtgtgtgt gtgtgtgtgt gtggtgtgtg tgtgtgtgtg     1320
tgtgtgtaga gagagagaga gagagagaaa atgagattga gaatcctcct tcttcatact     1380
cgaaccaaga aagagtatcc tggggtttgg gactgggatc ccgaggccga gtcccgccct     1440
cactctggtt ttaaagttga gaatgcagta tctcttggta tctccagaac ggattccttc     1500
cctaggtgta gggtgggccg gcaaagtcaa ccggccgctc tggatcatct gggaattcaa     1560
gagagcgatt ggagagaggt ctgatgtagc cacactgtct tgtcttgggg aaggccccag     1620
aagttccagg ctccattcca ggccctgtgt gggctcagt tgcccctctt aaggggtcag      1680
tgggacagtc cctctggggc tgcctctcac agggagttgt ccatgccatc ttggccttgg     1740
gcctagtgtc ctggcctggg ctgcctgctg ttctggccca atcatagcct ggagggaaag     1800
tcttctaatt gggctggagg ctccaggtcc cttaacgcat gcctcaaccc cgggtttctg     1860
tcctctgcct cccaccactc tggtgccgtc tgaattaccc tgctggggg acagcagtgg      1920 catactcatg cctaagtgac tggctttcac cccagtagtg attgccctcc atcaacactg     1980
cccaccccag gttggggcta ccccagccca tcttcacaaa acagggcaag gtgaactaat     2040
ggagtgggtg gaggagttgg aagaaatccc agcgtcagtc accgggatag aattcccaag     2100
gaaccctctt tttggaggat ggtttccatt tctggaggcg atctgccgac agggtgaatg     2160
ccttcttgct tgtcttctgg ggaatcagag agagtccgtt ttgtggtggg aagagtgtgg     2220
ctgtgtactt tgaactcctg taaattctct gactcatgtc cacaaaacca acagttttgt     2280
gaatgtgtct ggaggcaagg gaagggccac tcaggatcta tgttgaaggg aagaggcctg     2340
gggctggagt attcgcttcc taaagggcag tgtgaggtgg tggtgggtg tggggagtag      2400 aggcgttcag tcagcccagt ttgacaggat gtgggactga gagaaaagc taggtttgag      2460 gctgagatca ggttaccgtc gcttcttaa ctgctccctg cctggttggt gctgggactg      2520
gccctcattt gtctcttctt ttggggctcc tcccagccca gactctagcc ccctccccct     2580
tcccaacagc cttgacttca tctcagctcc agagcccgcc ctctcttcct gcagcctggg     2640
aacttcagcc ggctggaggt cagttcccct ccccagggaa ggaggaagtg agggaagctg     2700
cgaaggtgtg atgaactgtg cagatgctcg ctgtgtgtgc tgggggtggg ggacacatgg     2760
aagcccggga agctgactcc ttgccctgag tcacaggag gggtgggcag gcatgcggg       2820 tgagctggac tgaggaggga aggggctgtt ccagagtggg tggaggtgat tccctggtgg     2880
attcttctca gtcactgtgc tgtggtagat gtatggctcc ctacagtgtg gtcattgtcc     2940
cctgccgggg gctgagtgac ccagtgttgc tggcaggcct aggaggaagg ggggaggaag     3000
```

```
gcagcctgcc caaactcgag ctgtgggcat tgctgggact gagcctcctt tgtattactt    3060
ggggctttgg ggaccgggtg gggtggacca gggaagctgg ctggctgcta cccctgtcct    3120
ctgtctgggt ttccctgctt ctgctctccc tcctgcccct gaggtgacat gtcgaagagg    3180
cacgactttg agtcacacag tcctgctttg ggtgctgtcc ctgccccta taagccacag     3240 ctctgaatct gtgttaacct cactgagcct tagtttcctg gtttgtcaaa atggaaagtg    3300
caccatctac cttccaggca tctgggtacc gaaggagata attcctgcca aaatgcccga    3360
cagagtgcct ggcacctagg ggctctataa ctattcttcc tttacccacc taccacctgg    3420
tagctggttc tgctactctg gtcctagaga gggactcctc atttgtgact ggacaggtat    3480
gacttgtgct gagggacagt ctgttctaga ttggacctta gagattatta aactgtaaat    3540
gcatcaaaat cctggtaacc aatgaagtct gactcgaaac cctgatgtgt gaagtagata    3600
gaagcttgct ccctgacgt cccgcatccc tgagcagctc tctagctacc tggagtcccc     3660
aggttggcaa gtggattaga ttgaaactca tgttttccag ctcccaagtg gggtcatcat    3720
ctacctccca ccactgtatt ctaacccatc gagggagacc tgtccctgac ccagagatta    3780
ggaatttcaa gctctgttgt cgcacaattg gtgttttgcc agaacatgcc tgagcaagcc    3840
ccctgtccct ttgctagatg cctcggtttc cagggaggtt tgggggccct agagaagtgt    3900
ttttggactt aatggctttt cctcaaatcc ccaatacgtc tttcctggca gccccaccat    3960
ggctgcaatc cgaaagaagc tggtgatcgt tggggatggt gcctgtggga agacctgcct    4020
cctcatcgtc ttcagcaagg atcagttccc ggaggtctac gtccctactg tctttgagaa    4080
ctatattgcg gacattgagg tggacggcaa gcaggtgaag gcagaaatgc cttcccacc     4140 ccaccctgag tccccgcccc ccagtcactg aatgacctag tatgtccttc cccattccta    4200
cccctgtctt tgcttcattc tccctgctgg aaccagtaaa agttaggaag taaatctgca    4260
gtcttaaaaa acctggatat actttctggt tctcccacag actggctctg taacctgggc    4320
cgagtccctt tgcctctggg tttaagctcc cccacctgca aaatggggat gatggtaaga    4380
cctccctcaa agggttgttg tgagaattaa ccaaaataat ggtgctcaca gtggcaactc    4440
aagggtcaaa cacgtcttag atttctttaa caaactgacc taatttatgt tgtgggacag    4500
tgattaatat aatgcctggt gcatagcagg tgctcaaata aagaagttca gtgagcccga    4560
aggacagtgg tttcagggga cctttgggtg gcagggttgg ggccctcagg ccagctactc    4620
actggccctg tgtgtcaggt ggagctggct ctgtgggaca cagcagggca ggaagactat    4680
gatcgactgc ggcctctctc ctacccggac actgatgtca tcctcatgtg cttctccatc    4740
gacagccctg acagcctggg tgagggatt ggagggaggg gactgagaac cccttggaat    4800
cagccagagg tctcgtgcct tggcctgtct tcagtcatct tcagaggtgg gggtggggat    4860 gcagggagc actcaggccc tgttggtctc ctttactgtg gtaactggcc ctctgagggc    4920
atactactgt tgaggttttg agctgtgaaa gggaccatca tgctgaatgg cttctaagac    4980
tgctctggga agatgagggc cccccaggg gagctttcta gcttaagtgg aggcaccgac    5040
acctgttggt gcatgtctac acagaaaaca ttcctgagaa gtgaccccca gaggtgaagc    5100
acttctgccc caacgtgccc atcatcctgg tgggaataa gaaggacctg aggcaagacg     5160
agcacaccag gagagagctg gccaagatga agcaggtggg tacggctgcc aggctggagc    5220
ccctggggaa gaatgcaccc tctgaggggt tgcagacggg caaagggaac ttctctccag    5280
ctactgccgt gtgttagggg aaacagtaat atctcctggt gagggaggac ccataggttt    5340
gtgtctgatg aggtatcaga atgaagtgac ttgtccaaag tcacttggca tttttattta    5400
```

-continued

```
ttccagttaa ttgtccattc cgttcagaat tgggactatt aagatgatta agaaaatctg    5460
ccctcgggga gacagcttat gtttcacttg ggatacccag gctgtgccat cagagtgccc    5520 ctggggagg tgtagggatg tggatgcggg aatgagggca ggcattgtgt aagtggctgg     5580
aagaagggat gtgagagctg gcttattcag ggacctgtaa gtggctctct agccagagga    5640
ctagagttta ttagagaaag ctgtcaggat aagaaatgca aagataatta tggcaaagtt    5700
tcaaactggg gagatgttag gtctgtgtgt tagaaaaata attctgactg gaagagagtg    5760
aggatggagg cagagcagtc aggaggtggg agacgctcat tcaggcaaga gaaccagggg    5820
ctgtgtgtgg gaggaggtgg ggctgcatgg gaatggaggg agtagactgg agggattttt    5880
ggatccctgg ccacgaagct gcccagggta gctgggcct gggcgctttc tgggtcaggg     5940
ctggaggagg aggcatttgt tccagctgct acacttatgg gtgaggcagg agaggttcat    6000
gtagtcaaca gcttcctttg accctcatc ttatgtcttc tcaggagccc gttcggtctg     6060
aggaaggccg ggacatggcg aaccggatca gtgcctttgg ctaccttgag tgctcagcca    6120
agaccaagga gggagtgcgg gaggtgtttg agatggccac tcgggctggc ctccaggtcc    6180
gcaagaacaa gcgtcggagg ggctgtccca ttctctgaga tccccaaggc ctttcctaca    6240 tgcccctcc cttcacaggg gtacagaaat tatccccta caaccccagc ctcctgaggg      6300
ctccatgctg aaggctccca ttttcagttc cctcctgccc aggactgcat tgttttctag    6360
ccccgaggtg gtggcacggg ccctccctcc cagcgctctg ggagccacgc ctatgccctg    6420
cccttcctca gggcccctgg ggatcttgcc ccctttgacc ttccccaaag gatggtcaca    6480
caccagcact ttatacactt ttggctcaca ggaaagtgtc tgcagtaggg acccagagt     6540 cccaggccc tggagttgtt ttcggcaggg gccttgtctc tcactgcatt tggtcagggg    6600
ggcatgaata aaggctacag gctccaacgt gtgtggcagc tttcggtctt tccctctggg    6660
tgcttggtgt cccatctctt ttcatgtcca agttgcttgc cagcctggcc ccctgtctac    6720
aaagcaggcc agtggccagc agggtggagt cttagagcaa aggatgaggt catgcctggc    6780
tctgggccaa ggaggcgggt gaagggagtg gtctgtagca gggggctaaa cttagaaacc    6840
tgtgggtggc ttccctgcca cctcccactg ggtttcctcc cccgagtgtg ggggctgggt    6900
tcctctccag ctgggagggg atgtgaccct cagcagggct gaaagtccca cccttcccta    6960
cagggtcagc ttagggctc aggaagctgg ggccaggcag aggagacatt atcaaggctt     7020
ttgcatagaa caagattttg ttttcagagt tttcttcctt ccccttcccc caattgttag    7080
cagcttgatg tgtcattctc cccagcaggg gaggggtgg aatggcttgg gttgtaaact     7140
ccctccccca gccttcctgt cccttggagg ggcagttcag ctgggttctg gttcagggtc    7200
aggcaggcag ttaaggcttg gctggtgcga gaaggctggg tgctgtgtct tcagagctca    7260
ttcctccact ctggctccac ttgcagagac aggccccctt caccctcccg ctcctggggg    7320
aggtagtcat ggctgtgggg ccctggaaag agagaaagta cactgtgtct tccttaccac    7380
ctcctctggc actgtcccca ccctggccca gccatacctg aggtagaggg gctgagcttg    7440
ctcagacctt gcagtaaatt ctgtccctgt tgcaggtcca gtttggcagg gaagggacac    7500
ccggtatacc ctccgttttc tttacagaac tccaggaatc tgtggggtac agaggagtgc    7560
cagcagagac tggaggctaa gccacggtcc tgtcccatct gagctgtact tgctcaacct    7620
ctggatgtca tttaacttat aaatacaata gtgatgctgt gaaaatggac acatctgagg    7680
attaactgag cgataagcaa gcgcttaaaa aagatccacc tgcccctaggc aggggctgtg   7740 gccactaaga gggagaatgg ggtgggaatg ctcacacttt ccagtcaggg tcatggccca    7800
```

```
ggagaagggg gttccccacg atgatgagca gggccttggc ccgggtcaca gctacattga    7860
acctctggaa ggaagaagtg gtgtggtcat gagagggaag agccccgaga atggaagaat    7920
tcctgccacc ccgaccagcc ctcaaacctt ggggttctta aggaacccca gattaaagtc    7980
cagatccagc tgcacaaagc tctggctgct tcgcacggtg gagatgagga tgacgcttcg    8040
ttcttggcct tggaattctt ctactgaacc cacctagtgg ggaaagaggc agggcctgag    8100
accagccagg ggtgtcaaag gggtgcccta ccccagggag cttgccttcc aaggagggta    8160
cagagaggtc actgggcaat gtagatcag tgagtgaacc agtgctgcga cacgcccag    8220
ggaaagggga tgggaggtag gctgtggaag ctgaaacatg aaggttgaat cctgctgagg    8280
gctgggcct gcaaagtgtt ctaaggaaag aaaacagcat tgcaaagaac acgggaactc    8340
agagcagtga ctttcaaact ttcctgaaaa caatcactaa gtatctgtta agaatataca    8400
accctgggcc ctaacccgga cccccgatca gaatttccaa gagagaggcc tgtaagtctt    8460
agagcagtgt tttcaaccct ggctgcatat tagaatcacc tgagaagctg taaaaactac    8520
cagtgccctg gctctgcccc gatagctgta tgagctggtg ggtggggccc tggcatgggg    8580
gcggggtatt aaaagctctc caggtgattg ttatctgcag ccagtgttga gccagaacc    8640
ttaagagaga ggctactggg ggtgggggtg gcagcatcac atgacaggcc acggaatttg    8700
gactttatcc ttagggcaga ggcctcaaac ctgcctcagt ctaagaatga caggaggtgt    8760
ttgttaaaca tgcaggcttc ctgatcccat cccagaccct taagttggaa tctccaggag    8820
tgagaggctc agggagagct cgagctctat tcaaggcagc aggggtggga cggggacgtg    8880
ggctggagtg gaagcttgag gaagtctctg gaagtgggca agtggggca cacggaaggc    8940
agggagtgac tgtggaacag catgtcacct tcaagtcctt gatgtcatcc agtcctcgaa    9000
gctccctgtc aagtttggtg atgcagtaac ggattttctc cacctggaag gaggggacag    9060
gtgcctttct ctcgtgccat taacctaatg caagagggag cctggcagga ggccaggag    9120
ctggggaaca aagggaggcg gcagctgacc ttggtgctct tctgagatac ggagccagca    9180
gaggcctaag ctcctggagc ctctgcctag tggtctggat attaaggagg taccatctgg    9240
gggagggcc ccaccttgc tggtaactga ggacctgacc tgtttccggt acggggagat    9300
gacgcccaca cttcgagggc tcaggcgagc tttgccctc ttggaggagg gggccaggag    9360
cagcttcagg taggaagtca ctgtggcagc ctcttcaggg ttgaagaagg atgggctgtt    9420
gccttcacgc tcatctttgc ccattacgcc gtgaaagatg atgggaaagc cctggacatg    9480
gggtcggggg aaaccgtcag ccagaccacc cctccctcta ttccctccct tcccaaaccc    9540
ttccagagag taagagatcc taggccaagg tgacaaaggg aggggctgca ccttcagtgg    9600
gagggaagtc agggtacagg ggtggggcct gccctgctca gcctcacctg tcgaggtagg    9660
cccgcccagc ggcagaagcg ttctcgatcc acgacatcag cacaggcctg cagctcccct    9720
tcataataga gctggttagg aatgtccagg atggtgggat gagacctggg aggccggagg    9780
aggaaaagca agaccaaggg tcagattccc tctgccctac aggggctccg ctctacccac    9840
tctgggccca cacacaatag cctgctaccc cgctggctcc ctggatagca ggacactcct    9900
ccataatatc tgctgccagg cactgtaaac cacagaaagc agaaccaaat atagttccag    9960
agagcatcta gtccagggac tccacagacc catgacattt aaaactaaat aattagggc    10020
ccattttcag gtttcaaatt taccaaggac agtacgaaac caattctcc ttgactatca    10080
cgttatttga tgagaccatg tgttaaatca aaaaatataa gcagtgatga cacaataact    10140
aacatttatt gagctcttag tgacagcata aaacttatct aagcatttta gatggctgaa    10200
```

```
ctcattcact aaaagtatac agctctttaa tttgaataac aataggttta tgaaaaaact   10260
gtatcttccc tattttcctt tctttttttg agatggagtc tcgctctgtc acccaggcta   10320
gactgcagta gcgcgatctc agctcactgc aacctctgcc tcccgggtac aagcgattat   10380
cctgcctcag cctcccaagt aactggaatt acaggtgcct gtcactatgc ctggctaatt   10440
tttgtatttt tagtagagat ggggtttcac catgttggac aggctggtct caaactcctg   10500
acctcaagtg atcgggggtg ggagcctgac ctaccttggc ctcccaaagt gctgggatta   10560
cagccatgag ccactgtgcc cgacctcctc cctattttc ttatctctcc ttggattgcc   10620
tgaaaacttc atctgggact ggtaccagac acaccctagc ctttaggaac cactgaccac   10680
cccctaagat gcagataagc tgactggtgt agtgtgaaac cactggctaa gtcacgcaga   10740
caacaagcag cagtgctggg gctagaaaaa cctcctgcct tccagtttag tctttctgca   10800
tcacacaacc tctgagcaac aggactgaca gcaagccaga ctctccagtg ggtctgcat    10860 gcaggatgtg aaagcatagg atatggcagg ggaggcaagg gcgtgggaat acctgtagtt   10920
gcggagcagc ttggttatga actgggggtc atagccatca gggcccttct tgtacaggga   10980
gttgtaggtg agcagccgct ccagcagtga gtatcccagt ccatgcttct gggtcagtgg   11040
ggaacgcagc acaggcccca gctgccgagg gtctcctgcc agcaccagct gccctcctgg   11100
atcacctgtt tcctttactt ccatcagccc tgggaagcag aagaggtgtg ggaagaaagg   11160
taagtggtgc aacctctctg acccacacag ggtgtatacc tgcagcccca cctgagtccc   11220
tcacctgcta tagctaccag actctcaggc tccatgcagt ggccagcctc atcgatgaag   11280
atgtgtgtga agtgatcaat gggaaactgg gccgagacca acctgggagg tgtcaggcca   11340
ggcaggggtc atatccaggc acccaactac caaacctgaa tgctttccca ggctggcttc   11400
tcagcaccca ccaccccact ccggaaacca ttcttcccca tttccccagc ccggtacccc   11460
tttaattaca cttacgattc agagacacac ccacacacac tccccacctg ccggcagtga   11520
tgagggtggt aattaagacc cggtattcct gcagcttctt cttggcggga aatacatact   11580 ccccttctt tgcgtcccag ttgcagcagg gctgtggatt gtgaagggac cagaggaatc    11640
agcttggctc cactcattcc caccgtgatt ctggctgtgg gtaccccccc tcaaacaatt   11700 attttattt ttttaattg agacggagtc tcgctgtccc ccaggctgga gtgccatggt     11760
gtgatcttgg cccactgcaa cctccgccgc ctgggttcaa gcaattctcg tgcctcagcc   11820
tcccgagtag ctggggctac aggcacgcgc caccatactc agctgatttt tttgtatttt   11880
tagtagagac gggattttgc catgttggcc aggctggtct caaactccag acctcaggta   11940
atccatctgc ctcgcccctc aaagtgttgg gattacaagt gtaagccact gcacccagcc   12000
ccccaaatgt tttatccacc cccctcactt acagacaaac tgaggcccag ggaggggtcc   12060
tgtccaaccc aaggtcacat agcaagtatc agaatccagg tctcctagct tcctcgcctc   12120
agtgtctgcc ctgagagcct ccccggcatt tgccattctt tggccctctg cacttcccta   12180
gtaccttgat gtcctcaggt accatgcgga tgtccctgct gggggccagg aggcggtaga   12240
tggagctagg aaggtggacc cggagccttt gacagagtag gtcagcccct gagttggatg   12300
gagcgcaggc caagatgtgg gctttgggca agtgcttcac cacctgagat gcagataagc   12360
gcagtgtggg aggcaggttc ctgagactca gccgtaccca ggctggggca gggcaagtct   12420
atgatgactg aaatgtgaat ggtgactcca agattcatgc agtgccctac ccgtacaaca   12480
gtgctccaca gccacattta ccctaacttc ccacttcccc aatccccacc cttttttttg   12540
agacagagtc tcactctgtc acccaggatg gagtgcagtg gcacaatcgc actgcagcct   12600
```

```
caagtgccca gctatttttc atatttttca tagagatagg gtcttgcaat attgtccagg    12660
ctggtcttga actccttggg ctagtcttcc ccaagtgctg agattacagg catgagccac    12720
tgcacccggc ccctacctct ctttctgatg gctgcttaga agcaggagca tttcgggagt    12780
gggaaggaac tagaatctgg ggacaactgc ttggtgctgg gggaatcaga gtgcaggccc    12840
caggtttgtg ctcagacccc acctgcttaa ttgcctccac taacgtgaca gtcttgccgg    12900
tgcctggagg cccaaagatg atgtaggggg ctggacgggt ggtgcccgta acaatgtgcc    12960
tcatggcctg cagctgctct gggtttgact ccagactccg gtcgtacagc ctggcagagg    13020
gaccaggaat gtgaacttga agtcatccag tgacccagag gcctccctga ctccaccccc    13080
tgtgcccaca ctccaagtgg ctccagaagc tccctgccca cagtctcact tgagtttcac    13140
atctgagggc agcagcggga cgtcccgagg tgccacagga aagagcatgg gccacagcag    13200
ccagcgccct gtcagctcca gggcacggtg ctggactcgc agcggctggc ggttgaaggt    13260
aaagttcacc ttgaaggtca gcccatccac aaagcggctc aggaggcttt gggcagagag    13320
aggtggtaag agtttgttgg ggcagggagg gtgggcaata aagggccaga actttctcca    13380
ccaaccagtg tcccaacccc tctttccaag acctctatgc aagttctcta gaagaggaag    13440
ctgccgtagc atctcagggt acccctgagg aaaagtctcc tgctctgccc cggggtctca    13500
tttatctcag ggagaaacac tcctcctccc ctggggtcag aagtctgtag acccttccag    13560
cagctcaggg ttcccccaac acccacctca tggaaaagct cagcttgaca cggtccaatt    13620
ccaccttgtg cacaaagccc ttatatgtga tggggtcctc ctggtgtgtc tccgaggaca    13680
aaagggcaaa caggtggtcg ccccgtagca ctgaggggcg gctctcagtc actccaggaa    13740
cctatggggt gtgaacacaa gcaagcttct gtcccaggga tggacgctgg agggcccagc    13800
ccccaggttc cccagacctt taagggacaa ggactgagac tggccttcta acctaagact    13860
cagggagtta tgctatccct gcaccccctct ttcctttcat accagcagga gtcagggaa    13920 gaggaagaag acaaatcctc cgaagctgcc cagagatgct gagcccagga acccggagcc    13980
tccagtgcag ctgccctctt ggccagctca gttcctgctc tgcctataaa aatcctgttc    14040
atcagttaat cgggttgcta aaaaaataat ttaaaaaaaa aaaaaaaaa aacggaccag    14100 gcatggtggc tcacgcctgt aatcccagca ctttgggaga ctgaggcagg cggatcactt    14160
gagtccaggt gttgcgagac cagcctggcc aatgtggcaa acccccatct ctacaaaaaa    14220
tacaaaaatt agccaggcgt agtggggcat gtctgtggtc ccagctactt gggaggatca    14280
cttgagcccg ggcagcgggg attaaagcga gccaagatca tgccattgca ctccagcctg    14340
agcaccaggg tgagccctg tctcaaaaca aaaacaacaa caacaaaaaa cttgttcaaa    14400
actcacttcc tgcagtaatc tttccttgaa caaactcacc ctctaattcc cacctgcaat    14460
tgtgtgtaga aatccattct cgtgtgtaat tttgggctta tatgcacaca ttgaaaatcc    14520
aagagccaga aagagctcta agaattatcc agtccagctc tgtgcttttc agataaggga    14580
actaaggctt agagaaagcc agggacttac ccaaggtggt agcaaagcct ggactagaac    14640
ccagatcttc cccatttccc tgctccaaca catctttggg cacaggatgc ccaccctgct    14700
tcttgcggag ccctgggaac cacttcaact ttcctcttgt tctgccctgc tgtcaggaat    14760
agttctgccc acagcctcta gcttggctgg cttgagccca ccctcctcac actcaatctg    14820
agccctgacc tccagcgtga gcagcctggg gttctggtcc acagggtccc aggtcatggg    14880
caccgactcc aggtcatagt gccggatatc atgctccatc tgcagttcct ccaggtgcag    14940
cagcagccgc agcttcacct catagttcct ccacttcagg gctgtctcca gctgggccct    15000
```

```
ggaaatgatg gttgggaggg gtgagtgggg gcaggaacag gatgggccag acaaccccta   15060
tgcccaggag tatccacctt ctcccacctg aagctctgga actagcgtca aaaagcagag   15120
aagactagag ggatacagaa gtggatgaga gtcagaggcc ctgaagaagg aagccttggc   15180
tcctgcttcc ttggatgccc ctgcccccac ctcacccgac ttgcatttgc atggtggctc   15240
ttatggccag aacattctcc tccaatcctc tcatgactcc cacccctcacc tcattcaaat   15300 gtccttctct gttcaaacat cactacctca aacaggccag gactaactgg ccttctgcaa   15360
agcagcacca acccattccc taaccctgct ttagtttcag tatagttctg ttcatctttt   15420
ttagagacaa gatcttgctc tgtcacccat gctggagtgc agtggcatga tctgggctca   15480
ctcactgtgt cctcaacctc ctgggctcaa gaaattctcc cacctctgcc tcacaagtag   15540
ctgggactac agacatgtgc caccacactt ggctaattaa aatttttttt tgtagagaca   15600
gaatctcact atgttgcccc aggctggtct tgaactcttg ggcttaaatg atccacctgc   15660
ctcggcctcc caaagtgctg agattacagg catgagccac ttacacctga cctgtttagt   15720
tcttcacagc actcatcact ccatgaaatt gtaacaaaaa tgctcattgt cccccattaa   15780
aatgagccag gccttcattt gactggttca ccttgaatgg tgcttggtgt atggtgcgtg   15840
ctcagtaagg gaatgaatga atacagcctg ggaggctgag gacggaggtg ccagggcaat   15900
gcaaagaagc cagtaggtaa aagatgggag agtgcgggt gcagagggat ggtacttact   15960
tgatctctgc gatctcctta ggggcagtga agatacttgt tccctgaaga agcatgggga   16020
gcagctgcct gaggcgggga ggtgggtagt atgtccccag cgccatactt aactccaggt   16080
catagccctt agcgctgcag aatcgaggga agaaaacaca gaaaacccct ccccctcccc   16140
cactctgaga acgcccctct ggggtggatg cacaaagccc tcctgcaatc ctactgctga   16200
agggaagtca gcagcctcgc tccaagggtg gactactctc attttggaa catgcgatac   16260 ttggaaacct ttaaaactat tatctaagta ataaatgatc actagagaaa aaaatcaggt   16320
aataggtaat aagtaaatat cattctt                                      16347
```

US 8,053,195 B1

ISOLATED GENOMIC NUCLEIC ACID MOLECULES OBTAINABLE FROM CHROMOSOME 1P21-P13 THAT ENCODE HUMAN RHOC

PRIORITY CLAIM

This application claims priority from application Ser. No. 60/418,034, filed Oct. 12, 2002 under 35 U.S.C. 119(e), the contents of which are incorporated herein by reference.

FIELD OF THE INVENTION

The invention is directed to isolated genomic nucleic acid molecule fragments that encode human RhoC, vectors and hosts containing these fragments and fragments hybridizing to noncoding regions as well as antisense oligonucleotides to these fragments. The invention is further directed to methods of using these fragments to obtain human RhoC and to diagnose, treat, prevent and/or ameliorate a pathological disorder.

BACKGROUND OF THE INVENTION

Chromosome 1p21-p13 contains genes encoding, for example, adenosine monophosphate deaminase-1, macrophage colony-stimulating factor-1, RAS-related protein RAP1A, beta nerve growth factor and RhoC; the last of which will be discussed in detail below. Mutations in the chromosome 1p21-p13 region are associated with some forms of colorectal cancer and Waardenburg syndrome type 2B.

Human RhoC

Human RhoC, is a member of the Ras superfamily of GTP-binding proteins involved in signal transduction, cell proliferation, vesicle trafficking and regulation of the actin cytoskeleton. RhoC possesses GTPase enzymic activity. Recently, several investigators have found that RhoC is up-regulated in some metastatic tumors. Specifically, RhoC appears to be a transforming oncogene in the inflammatory breast cancer phenotype (van Golen et al., Cancer Res. 60: 5832-8, 2000). Overexpression of the RhoC gene is also correlated with progression of ductal adenocarcinoma of the pancreas (Suwa et al., Br. J. Cancer 77: 147-52, 1998). Clark et al. (Nature 406: 532-5) have reported that overexpression of RhoC in melanoma cells enhances metastasis.

OBJECTS OF THE INVENTION

Although cDNA encoding the above-disclosed protein, RhoC, has been isolated (e.g. see accession no. L25081), its exact location on chromosome 1p21-p13 and exon/intron/regulatory organization have not been determined. Furthermore, genomic DNA encoding the polypeptide has not been isolated. Noncoding sequences play a significant role in regulating the expression of polypeptides as well as the processing of RNA encoding these polypeptides.

There is clearly a need for obtaining genomic nucleic acid molecule sequences encoding the RhoC polypeptide. Therefore, it is an object of the invention to isolate such genomic nucleic acid molecule sequences.

There is also a need to develop means for identifying mutations, duplications, translocations, polysomies and mosaicism as may affect the RhoC gene.

SUMMARY OF THE INVENTION

The invention is directed to an isolated genomic nucleic acid molecule, said nucleic acid molecule obtainable from human chromosome 1 having a nucleotide sequence at least 95% identical to a sequence selected from the group consisting of:
   a) a genomic nucleic acid molecule encoding human RhoC depicted in SEQ ID NO:1 or variants of SEQ ID NO:1;
   b) a genomic nucleic acid molecule consisting of SEQ ID NO:2, which encodes human RhoC depicted in SEQ ID NO:1 or variants of SEQ ID NO:2;
   c) a nucleic acid molecule that hybridizes to any one of the nucleic acid molecules specified in a)-b);
   d) a nucleic acid molecule that is a reverse complement of the nucleic acid molecules specified in a)-c);
as well as nucleic acid constructs, expression vectors and host cells containing these nucleic acid molecule sequences.

The nucleic acid molecules of the present invention may be used for the manufacture of a gene therapy for the prevention, treatment or amelioration of a medical condition by adding an amount of a composition comprising said nucleic acid molecule effective to prevent, treat or ameliorate said medical condition.

The invention is further directed to obtaining human RhoC or variant thereof comprising:
   (a) culturing host cells comprising these sequences under conditions that provide for the expression of said polypeptide and
   (b) recovering said expressed polypeptide.

The polypeptides obtained may be used to produce antibodies by
   (a) optionally conjugating said polypeptide to a carrier protein;
   (b) immunizing a host animal with said polypeptide or peptide-carrier protein conjugate of step (a) with an adjuvant and
   (c) obtaining antibody from said immunized host animal.

The invention is further directed to a nucleic acid molecule of at least 15 nucleotides or reverse complement thereof including but not limited to a polynucleotide fragment, antisense oligonucleotide or antisense mimetic comprising a sequence of nucleotides that specifically hybridizes to noncoding regions of said polynucleotide sequence of SEQ ID NO:2 (human RhoC gene). These sequences may be used to modulate levels of human RhoC in a subject in need thereof and specifically for the manufacture of a medicament for prevention, treatment or amelioration of a medical condition. As defined herein, a "polynucleotide fragment" may be a nucleic acid molecule including DNA, RNA and analogs thereof including peptide nucleic acids and mixtures thereof and may include a probe and primer. "The term 'polynucleotide' or "polynucleotide fragment" encompasses nucleic acid sequences of 15 or more nucleotides specific to the RhoC gene. Such molecules are generally of a length such that they are statistically unique in the genome of interest. Generally, for a probe or primer to be unique in the human genome, it contains at least 15, 16, 17, 18 or 19 nucleotides of a sequence complementary to or identical to a target sequence of interest. These polynucleotide fragments can be 20, 30, 50, 100, 150, 500, 600, 1,000, 2,000 or more nucleotides long. Probes and primers may also be referred to as oligonucleotides. As defined herein, an "antisense oligonucleotide" is a molecule encoding a sequence complementary to at least a portion of an RNA molecule. The sequence is sufficiently complementary to be able to hybridize with the RNA, preferably under moderate or high stringency conditions to form a stable duplex or triplex. A "reverse complement" also includes peptide nucleic acid reverse complement sequences.

The invention is further directed to kits comprising these nucleic acid molecules. In one specific embodiment, the sequence(s) are attached to a substrate. In another specific embodiment, the support is a microarray. The microarray may contain a plurality of sequences hybridizing to non-coding sequences. As defined herein, a "plurality" of sequences is two or more sequences. Alternatively, the microarray comprises non-coding sequences as well as coding sequences.

In a specific embodiment, the non-coding regions are transcription regulatory regions, The transcription regulatory regions may be used to produce a heterologous peptide by expressing in a host cell said transcription regulatory region operably linked to a polynucleotide encoding the heterologous polypeptide and recovering the expressed heterologous polypeptide.

The nucleic acid molecules of the present invention may be used to detect a pathological condition or susceptibility to a pathological condition in a subject comprising
 (a) isolating genomic DNA from said subject;
 (b) detecting the presence or absence of a variant in said genomic DNA using a probe or primer derived from a nucleic acid molecule hybridizing to non-coding region(s) of said human RhoC gene; and
 (c) diagnosing a pathological condition or susceptibility to a pathological condition based on the presence or absence of said variant.

Probes or primers derived from SEQ ID NO:2 (human RhoC gene) may be used to identify variants including but not limited to mutations, duplications, translocations, polysomies and mosaicism of the human RhoC gene and may be used to identify patients with or having a propensity for conditions in which RhoC is deficient or produced in excess. Furthermore probes or primers comprising at least 15 contiguous nucleotides that hybridizes to a noncoding region of SEQ ID NO:2 may be used to detect the presence or absence of a nucleic acid sequence encoding human RhoC in a sample.

DETAILED DESCRIPTION OF THE INVENTION

The invention is directed to isolated genomic nucleic acid molecules that encode human RhoC, which in a specific embodiment is the human RhoC gene, as well as vectors and hosts containing these fragments and polynucleotide fragments or reverse complement thereof hybridizing to noncoding regions, as well.

As defined herein, a "gene" is the segment of DNA involved in producing a polypeptide chain; it includes regions preceding and following the coding region, as well as intervening sequences (introns) between individual coding segments (exons).

As defined herein "isolated" refers to material removed from its original environment and is thus altered "by the hand of man" from its natural state. An isolated polynucleotide can be part of a vector, a composition of matter or can be contained within a cell as long as the cell is not the original environment of the polynucleotide.

The polynucleotides of the present invention may be in the form of RNA or in the form of DNA, which DNA includes genomic DNA and synthetic DNA. The DNA may be double-stranded or single-stranded and if single stranded may be the coding strand or non-coding strand. The human RhoC gene is 16347 base pairs in length and contains 4 exons (see Table 1 below for location of exons). As will be discussed in further detail below, the gene is situated in genomic clone AC024481.

The polynucleotides of the invention have at least a 95% identity and may have a 96%, 97%, 98% or 99% identity to the polynucleotides depicted in SEQ ID NO:2 as well as the polynucleotides in reverse sense orientation, or the polynucleotide sequences encoding the human RhoC polypeptide depicted in SEQ ID NO:1.

A polynucleotide having 95% "identity" to a reference nucleotide sequence of the present invention, is identical to the reference sequence except that the polynucleotide sequence may include, on average, up to five point mutations per each 100 nucleotides of the reference nucleotide sequence encoding the polypeptide. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. The query sequence may be an entire sequence, the ORF (open reading frame), or any fragment specified as described herein.

As a practical matter, whether any particular nucleic acid molecule or polypeptide is at least 90%, 95%, 96%, 97%, 98% or 99% identical to a nucleotide sequence of the presence invention can be determined conventionally using known computer programs. A preferred method for determining the best overall match between a query sequence (a sequence of the present invention) and a subject sequence, also referred to as a global sequence alignment, can be determined using the FASTDB computer program based on the algorithm of Brutlag et al. (Comp. App. Biosci. (1990) 6:237-245). In a sequence alignment the query and subject sequences are both DNA sequences. An RNA sequence can be compared by converting U's to T's. The result of said global sequence alignment is in percent identity. Preferred parameters used in a FASTDB alignment of DNA sequences to calculate percent identity are: Matrix=Unitary, k-tuple=4, Mismatch Penalty=1, Joining Penalty=30, Randomization Group Length=0, Cutoff Score=1, Gap Penalty=5, Gap Size Penalty=0.05, Window Size=500 or the length of the subject nucleotide sequence, whichever is shorter.

If the subject sequence is shorter than the query sequence because of 5' or 3' deletions, not because of internal deletions, a manual correction must be made to the results. This is because the FASTDB program does not account for 5' and 3' truncations of the subject sequence when calculating percent identity. For subject sequences truncated at the 5' or 3' ends, relative to the query sequence, the percent identity is corrected by calculating the number of bases of the query sequence that are 5' and 3' of the subject sequence, which are not matched/aligned, as a percent of the total bases of the query sequence. Whether a nucleotide is matched/aligned is determined by results of the FASTDB sequence alignment. This percentage is then subtracted from the percent identify, calculated by the above FASTDB program using the specified parameters, to arrive at a final percent identity score. This corrected score is what is used for the purposes of the present invention. Only bases outside the 5' and 3' bases of the subject sequence, as displayed by the FASTDB alignment, which are not matched/aligned with the query sequence are calculated for the purposes of manually adjusting the percent identity score.

For example, a 90 base subject sequence is aligned to a 100 base query sequence to determine percent identity. The deletions occur at the 5' end of the subject sequence and therefore, the FASTDB alignment does not show a matched/alignment of the first 10 bases at 5' end. The 10 unpaired bases represent 10% of the sequence (number of bases at the 5' and 3' ends not matched/total numbers of bases in the query sequence) so 10% is subtracted from the percent identity score calculated by the FASTDB program. If the remaining 90 bases were perfectly matched the final percent identity would be 90%. In another example, a 90 base subject sequence is compared with a 100 base query sequence. This time the deletions are internal deletions so that there are no bases on the 5' or 3' of the subject sequence, which are not matched/aligned with the query. In this case the percent identity calculated by FASTDB is not manually corrected. Once again, only bases 5' and 3' of the subject sequence which are not matched/aligned with the query sequence are manually corrected for. No other manual corrections are made for purposes of the present invention.

A polypeptide that has an amino acid sequence at least, for example, 95% "identical" to a query amino acid sequence is identical to the query sequence except that the subject polypeptide sequence may include on average, up to five amino acid alterations per each 100 amino acids of the query amino acid sequence. In other words, to obtain a polypeptide having an amino acid sequence at least 95% identical to a query amino acid sequence, up to 5% of the amino acid residues in the subject sequence may be inserted, deleted, (indels) or substituted with another amino acid. These alterations of the reference sequence may occur at the amino or carboxy terminal positions of the reference amino acid sequence or anywhere between those terminal positions interspersed either individually among residues in the referenced sequence or in one or more contiguous groups within the reference sequence.

A preferred method for determining the best overall match between a query sequence (a sequence of the present invention) and a subject sequence, also referred to as a global sequence alignment, can be determined using the FASTDB computer program based on the algorithm of Brutlag et al. (Corn. App. Biosci. (1990) 6:237-245). In a sequence alignment, the query and subject sequence are either both nucleotide sequences or both amino acid sequences. The result of said global sequence alignment is in percent identity. Preferred parameters used in a FASTDB amino acid alignment are: Matrix=PAM 0, k-tuple=2, Mismatch Penalty=1, Joining Penalty=20, Randomization Group Length=0, Cutoff Score=1, Window Size=sequence length, Gap Penalty=5, Gap Size Penalty=0.05, Window Size=500 or the length of the subject amino acid sequence, whichever is shorter.

If the subject sequence is shorter than the query sequence due to N- or C-terminal deletions, not because of internal deletions, a manual correction must be made to the results. This is because the FASTDB program does not account for N- and C-terminal truncations of the subject sequence when calculating global percent identity. For subject sequences truncated at the N- and C-termini, relative to the query sequence, the percent identity is corrected by calculating the number of residues of the query sequence that are N- and C-terminal of the subject sequence, which are not matched/aligned with a corresponding subject residue, as a percent of the total bases of the query sequence. Whether a residue is matched/aligned is determined by results of the FASTDB sequence alignment. This percentage is then subtracted from the percent identity, calculated by the above FASTDB program using the specified parameters, to arrive at a final percent identity score. This final percent identity score is what is used for the purposes of the present invention. Only residues to the N- and C-termini of the subject sequence, which are not matched/aligned with the query sequence, are considered for the purposes of manually adjusting the percent identity score. That is, only query residue positions outside the farthest N- and C-terminal residues of the subject sequence.

The invention also encompasses polynucleotides that hybridize to the polynucleotides depicted in SEQ ID NO: 2. A polynucleotide "hybridizes" to another polynucleotide, when a single-stranded form of the polynucleotide can anneal to the other polynucleotide under the appropriate conditions of temperature and solution ionic strength (see Sambrook et al., supra). The conditions of temperature and ionic strength determine the "stringency" of the hybridization. For preliminary screening for homologous nucleic acids, low stringency hybridization conditions, corresponding to a temperature of 42° C., can be used, e.g., 5×SSC, 0.1% SDS, 0.25% milk, and no formamide; or 40% formamide, 5×SSC, 0.5% SDS). Moderate stringency hybridization conditions correspond to a higher temperature of 55° C., e.g., 40% formamide, with 5× or 6×SSC. High stringency hybridization conditions correspond to the highest temperature of 65° C., e.g., 50% formamide, 5× or 6×SSC. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA:RNA, DNA:RNA, DNA:DNA.

Polynucleotide and Polypeptide Variants

The invention is directed to both polynucleotide and polypeptide variants. A "variant" refers to a polynucleotide or polypeptide differing from the polynucleotide or polypeptide of the present invention, but retaining essential properties thereof.

The variants may contain alterations in the coding regions, non-coding regions, or both. Especially preferred are polynucleotide variants containing alterations that produce silent substitutions, additions, or deletions, but do not alter the properties or activities of the encoded polypeptide. Nucleotide variants produced by silent substitutions due to the degeneracy of the genetic code are preferred. Moreover, variants in which 5-10, 1-5, or 1-2 amino acids are substituted, deleted, or added in any combination are also preferred.

The invention also encompasses allelic variants of said polynucleotides. An allelic variant denotes any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

The amino acid sequences of the variant polypeptides may differ from the amino acid sequences depicted in SEQ ID NO:1 by an insertion or deletion of one or more amino acid residues and/or the substitution of one or more amino acid residues by different amino acid residues. Preferably, amino acid changes are of a minor nature, that is conservative amino acid substitutions that do not significantly affect the folding and/or activity of the protein; small deletions, typically of one to about 30 amino acids; small amino- or carboxyl-terminal extensions, such as an amino-terminal methionine residue; a small linker peptide of up to about 20-25 residues; or a small extension that facilitates purification by changing net charge or another function, such as a poly-histidine tract, an antigenic epitope or a binding domain.

Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions which do not generally alter the specific activity are known in the art and are described, for example, by H. Neurath and R. L. Hill, 1979, In, The Proteins, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, as well as these in reverse.

Noncoding Regions

The invention is further directed to polynucleotide fragments containing or hybridizing to noncoding regions of the human RhoC gene. These include but are not limited to an intron, a 5'-non-coding region, a 3'-non-coding region and splice junctions (see Table 1), as well as transcription factor binding sites (see Table 2). The polynucleotide fragments may be a short polynucleotide fragment which is at least 15, 16, 17, 18 or 19 nucleotides in length but may be between about 20 nucleotides to about 50 nucleotides in length. Such shorter fragments may be useful for diagnostic purposes. Such short polynucleotide fragments are also preferred with respect to polynucleotides containing or hybridizing to polynucleotides containing splice junctions. Alternatively larger fragments, e.g., of about 50, 150, 500, 600 or about 2000 nucleotides in length may be used.

TABLE 1

Exon/Intron Regions of the Human RhoC Gene in Genomic SEQ ID NO:2.

| Exons | Nucleotide no. | Peptide amino acid no. |
| --- | --- | --- |
| 1 | 3959-4111 | 1-51 |
| 2 | 4636-4758 | 52-92 |
| 3 | 5064-5192 | 93-135 |
| 4 | 6042-6215 | 136-193 | stop codon 6216-8

TABLE 2

Transcription Factor Binding Sites of the Human RhoC Gene.

| Sites | No. of Sites |
| --- | --- |
| AP1_C | 4 |
| AP1_Q2 | 2 |
| AP4_Q5 | 3 |
| AP4_Q6 | 2 |
| DELTAEF1_01 | 3 |
| GATA1_04 | 2 |
| GATA_C | 1 |
| LMO2COM_01 | 3 |
| LMO2COM_02 | 3 |
| LYF1_01 | 3 |
| MYOD_Q6 | 7 |
| MZF1_01 | 21 |
| NKX25_01 | 6 |
| S8_01 | 2 |
| SOX5_01 | 7 |
| TATA_C | 1 |
| TCF11_01 | 11 |

In a specific embodiment, such noncoding sequences are expression control sequences. These include but are not limited to DNA regulatory sequences, such as promoters, enhancers, repressors, terminators, and the like, that provide for the regulation of expression of a coding sequence in a host cell. In eukaryotic cells, polyadenylation signals are also control sequences.

In a more specific embodiment of the invention, the expression control sequences may be operatively linked to a polynucleotide encoding a heterologous polypeptide. Such expression control sequences may be about 50-200 nucleotides in length and specifically about 50, 100, 200, 500, 600, 1000 or 2000 nucleotides in length. A transcriptional control sequence is "operatively linked" to a polynucleotide encoding a heterologous polypeptide sequence when the expression control sequence controls and regulates the transcription and translation of that polynucleotide sequence. The term "operatively linked" includes having an appropriate start signal (e.g., ATG) in front of the polynucleotide sequence to be expressed and maintaining the correct reading frame to permit expression of the DNA sequence under the control of the expression control sequence and production of the desired product encoded by the polynucleotide sequence. If a gene that one desires to insert into a recombinant DNA molecule does not contain an appropriate start signal, such a start signal can be inserted upstream (5') of and in reading frame with the gene.

The invention is further directed to antisense oligonucleotides and mimetics to these polynucleotide sequences. Antisense technology can be used to control gene expression through triple-helix formation or antisense DNA or RNA, both of which methods are based on binding of a polynucleotide to DNA or RNA. For example, the 5' coding portion of the polynucleotide sequence, which encodes the mature polypeptides of the present invention, is used to design an antisense RNA oligonucleotide of from about 10 to 40 base pairs in length. A DNA oligonucleotide is designed to be complementary to a region of the gene involved in transcription or RNA processing (triple helix (see Lee et al., Nucl. Acids Res., 6:3073 (1979); Cooney et al, Science, 241:456 (1988); and Dervan et al., Science, 251: 1360 (1991)), thereby preventing transcription and the production of said polypeptides.

Expression of Polypeptides

Isolated Polynucleotide Sequences

The human chromosome genomic clone of accession number AC024481 has been discovered to contain the human RhoC gene by Genscan analysis (Burge et al., 1997, J. Mol. Biol. 268:78-94), BLAST2 and TBLASTN analysis (Altschul et al., 1997, Nucl. Acids Res. 25:3389-3402), in which the sequence of AC024481 was compared to the human RhoC cDNA sequence, accession number L25081.

The cloning of the nucleic acid sequences of the present invention from such genomic DNA can be effected, e.g., by using the well known polymerase chain reaction (PCR) or antibody screening of expression libraries to detect cloned DNA fragments with shared structural features. See, e.g., Innis et al., 1990, *PCR: A Guide to Methods and Application*, Academic Press, New York. Other nucleic acid amplification procedures such as ligase chain reaction (LCR), ligated activated transcription (LAT) and nucleic acid sequence-based amplification (NASBA) or long range PCR may be used. In a specific embodiment, 5'- or 3'-non-coding portions of the gene may be identified by methods including but are not limited to, filter probing, clone enrichment using specific probes and protocols similar or identical to 5'- and 3'-"RACE" protocols which are well known in the art. For instance, a method similar to 5'-RACE is available for generating the missing 5'-end of a desired full-length transcript. (Fromont-Racine et al., 1993, Nucl. Acids Res. 21:1683-1684).

Once the DNA fragments are generated, identification of the specific DNA fragment containing the desired human RhoC gene may be accomplished in a number of ways. For example, if an amount of a portion of a human RhoC gene or its specific RNA, or a fragment thereof, is available and can be purified and labeled, the generated DNA fragments may be screened by nucleic acid hybridization to the labeled probe (Benton and Davis, 1977, Science 196:180; Grunstein and Hogness, 1975, Proc. Natl. Acad. Sci. U.S.A. 72:3961). The present invention provides such nucleic acid probes, which can be conveniently prepared from the specific sequences disclosed herein, e.g., a hybridizable probe having a nucleotide sequence corresponding to at least a 10, and preferably a 15, nucleotide fragment of the sequences depicted in SEQ ID NO:2. Preferably, a fragment is selected that is highly unique to the polypeptides of the invention. Those DNA fragments with substantial homology to the probe will hybridize. As noted above, the greater the degree of homology, the more stringent hybridization conditions can be used. In one embodiment, low stringency hybridization conditions are used to identify a homologous human RhoC polynucleotide. However, in a preferred aspect, and as demonstrated experimentally herein, a nucleic acid encoding a polypeptide of the invention will hybridize to a nucleic acid derived from the polynucleotide sequence depicted in SEQ ID NO:2 or a hybridizable fragment thereof, under moderately stringent conditions; more preferably, it will hybridize under high stringency conditions.

Alternatively, the presence of the gene may be detected by assays based on the physical, chemical, or immunological properties of its expressed product. For example, cDNA clones, or DNA clones which hybrid-select the proper mRNAs, can be selected which produce a protein that, e.g., has similar or identical electrophoretic migration, isoelectric focusing behavior, proteolytic digestion maps, or antigenic properties as known for the human RhoC polynucleotide.

A gene encoding human RhoC polypeptide can also be identified by mRNA selection, i.e., by nucleic acid hybridization followed by in vitro translation. In this procedure, fragments are used to isolate complementary mRNAs by hybridization. Immunoprecipitation analysis or functional assays of the in vitro translation products of the products of the isolated mRNAs identifies the mRNA and, therefore, the complementary DNA fragments, that contain the desired sequences.

Nucleic Acid Constructs

The present invention also relates to nucleic acid constructs comprising a polynucleotide sequence containing the exon/intron segments of the human RhoC gene (nucleotides 3959-6218 of SEQ ID NO:2) operably linked to one or more control sequences which direct the expression of the coding sequence in a suitable host cell under conditions compatible with the control sequences. Expression will be understood to include any step involved in the production of the polypeptide including, but not limited to, transcription, post-transcriptional modification, translation, post-translational modification, and secretion.

The invention is further directed to a nucleic acid construct comprising expression control sequences derived from SEQ ID NO: 2 and a heterologous polynucleotide sequence.

"Nucleic acid construct" is defined herein as a nucleic acid molecule, either single- or double-stranded, which is isolated from a naturally occurring gene or which has been modified to contain segments of nucleic acid which are combined and juxtaposed in a manner which would not otherwise exist in nature. The term nucleic acid construct is synonymous with the term expression cassette when the nucleic acid construct contains all the control sequences required for expression of a coding sequence of the present invention. The term "coding sequence" is defined herein as a portion of a nucleic acid sequence which directly specifies the amino acid sequence of its protein product. The boundaries of the coding sequence are generally determined by a ribosome binding site (prokaryotes) or by the ATG start codon (eukaryotes) located just upstream of the open reading frame at the 5'-end of the mRNA and a transcription terminator sequence located just downstream of the open reading frame at the 3'-end of the mRNA. A coding sequence can include, but is not limited to, DNA, cDNA, and recombinant nucleic acid sequences.

The isolated polynucleotide of the present invention may be manipulated in a variety of ways to provide for expression of the polypeptide. Manipulation of the nucleic acid sequence prior to its insertion into a vector may be desirable or necessary depending on the expression vector. The techniques for modifying nucleic acid sequences utilizing recombinant DNA methods are well known in the art.

The control sequence may be an appropriate promoter sequence, a nucleic acid sequence which is recognized by a host cell for expression of the nucleic acid sequence. The promoter sequence contains transcriptional control sequences that regulate the expression of the polynucleotide. The promoter may be any nucleic acid sequence that shows transcriptional activity in the host cell of choice including mutant, truncated, and hybrid promoters, and may be obtained from genes encoding extracellular or intracellular polypeptides either homologous or heterologous to the host cell.

Examples of suitable promoters for directing the transcription of the nucleic acid constructs of the present invention, especially in a bacterial host cell, are the promoters obtained from the *E. coli* lac operon, the *Streptomyces coelicolor* agarase gene (dagA), the *Bacillus subtilis* levansucrase gene (sacB), the *Bacillus licheniformis* alpha-amylase gene (amyL), the *Bacillus stearothermophilus* maltogenic amylase gene (amyM), the *Bacillus amyloliquefaciens* alpha-amylase gene (amyQ), the *Bacillus licheniformis* penicillinase gene (penP), the *Bacillus subtilis* xylA and xylB genes, and the prokaryotic beta-lactamase gene (VIIIa-Komaroff et al., 1978, *Proceedings of the National Academy of Sciences USA* 75: 3727-3731), as well as the tac promoter (DeBoer et al., 1983, *Proceedings of the National Academy of Sciences USA* 80: 21-25). Further promoters are described in "Useful proteins from recombinant bacteria" in *Scientific American*, 1980, 242: 74-94; and in Sambrook et al., 1989, supra.

Examples of suitable promoters for directing the transcription of the nucleic acid constructs of the present invention in a filamentous fungal host cell are promoters obtained from the genes encoding *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, *Fusarium oxysporum* trypsin-like protease (WO 96/00787), NA2-tpi (a hybrid of the promoters from the genes encoding *Aspergillus niger* neutral alpha-amylase and *Aspergillus oryzae* triose phosphate isomerase), and mutant, truncated, and hybrid promoters thereof.

In a yeast host, useful promoters are obtained from the *Saccharomyces cerevisiae* enolase (ENO-1) gene, the *Saccharomyces cerevisiae* galactokinase gene (GAL1), the *Saccharomyces cerevisiae* alcohol dehydrogenase/glyceraldehyde-3-phosphate dehydrogenase genes (ADH2/GAP), and the *Saccharomyces cerevisiae* 3-phosphoglycerate kinase gene. Other useful promoters for yeast host cells are described by Romanos et al., 1992, *Yeast* 8: 423-488.

The control sequence may also be a suitable transcription terminator sequence, a sequence recognized by a host cell to terminate transcription. The terminator sequence is operably linked to the 3'-terminus of the nucleic acid sequence encoding the polypeptide. Any terminator which is functional in the host cell of choice may be used in the present invention.

Preferred terminators for filamentous fungal host cells are obtained from the genes encoding *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease.

Preferred terminators for yeast host cells are obtained from the genes encoding *Saccharomyces cerevisiae* enolase, *Saccharomyces cerevisiae* cytochrome C (CYC1), or *Saccharomyces cerevisiae* glyceraldehyde-3-phosphate dehydrogenase. Other useful terminators for yeast host cells are described by Romanos et al., 1992, supra.

The control sequence may also be a suitable leader sequence, a nontranslated region of an mRNA which is important for translation by the host cell. The leader sequence is operably linked to the 5'-terminus of the nucleic acid sequence encoding the polypeptide. Any leader sequence that is functional in the host cell of choice may be used in the present invention.

Preferred leaders for filamentous fungal host cells are obtained from the genes encoding *Aspergillus oryzae* TAKA amylase and *Aspergillus nidulans* triose phosphate isomerase.

Suitable leaders for yeast host cells are obtained from the *Saccharomyces cerevisiae* enolase (ENO-1) gene, the *Saccharomyces cerevisiae* 3-phosphoglycerate kinase gene, the *Saccharomyces cerevisiae* alpha-factor, and the *Saccharomyces cerevisiae* alcohol dehydrogenase/glyceraldehyde-3-phosphate dehydrogenase genes (ADH2/GAP).

The control sequence may also be a polyadenylation sequence, a sequence which is operably linked to the 3'-terminus of the nucleic acid sequence and which, when transcribed, is recognized by the host cell as a signal to add polyadenosine residues to transcribed mRNA. Any polyadenylation sequence which is functional in the host cell of choice may be used in the present invention.

Preferred polyadenylation sequences for filamentous fungal host cells are obtained from the genes encoding *Aspergillus oryzae* TAKA amylase, *Aspergillus niger* glucoamylase, *Aspergillus nidulans* anthranilate synthase, and *Aspergillus niger* alpha-glucosidase.

Useful polyadenylation sequences for yeast host cells are described by Guo and Sherman, 1995, *Molecular Cellular Biology* 15: 5983-5990.

The control sequence may also be a signal peptide coding region, which codes for an amino acid sequence linked to the amino terminus of the polypeptide which can direct the encoded polypeptide into the cell's secretory pathway. The 5'-end of the coding sequence of the nucleic acid sequence may inherently contain a signal peptide-coding region naturally linked in translation reading frame with the segment of the coding region which encodes the secreted polypeptide. Alternatively, the 5'-end of the coding sequence may contain a signal peptide coding region which is foreign to the coding sequence. The foreign signal peptide-coding region may be required where the coding sequence does not normally contain a signal peptide-coding region. Alternatively, the foreign signal peptide-coding region may simply replace the natural signal peptide-coding region in order to obtain enhanced secretion of the polypeptide. However, any signal peptide-coding region which directs the expressed polypeptide into the secretory pathway of a host cell of choice may be used in the present invention.

An effective signal peptide coding region for bacterial host cells is the signal peptide coding region obtained from the maltogenic amylase gene from *Bacillus* NCIB 11837, the *Bacillus stearothermophilus* alpha-amylase gene, the *Bacillus licheniformis* subtilisin gene, the *Bacillus licheniformis* beta-lactamase gene, the *Bacillus stearothermophilus* neutral proteases genes (nprT, nprS, nprM), or the *Bacillus subtilis* prsA gene. Further signal peptides are described by Simonen and Palva, 1993, *Microbiological Reviews* 57: 109-137.

An effective signal peptide coding region for filamentous fungal host cells is the signal peptide coding region obtained from the *Aspergillus oryzae* TAKA amylase gene, *Aspergillus niger* neutral amylase gene, *Aspergillus niger* glucoamylase gene, *Rhizomucor miehei* aspartic proteinase gene, *Humicola lanuginosa* cellulase gene, or *Humicola lanuginosa* lipase gene.

Useful signal peptides for yeast host cells are obtained from the genes for *Saccharomyces cerevisiae* alpha-factor and *Saccharomyces cerevisiae* invertase. Other useful signal peptide coding regions are described by Romanos et al., 1992, supra.

The control sequence may also be a propeptide coding region, which codes for an amino acid sequence positioned at the amino terminus of a polypeptide. The resultant polypeptide is known as a proenzyme or propolypeptide (or a zymogen in some cases). A propolypeptide is generally inactive and can be converted to a mature active polypeptide by catalytic or autocatalytic cleavage of the propeptide from the propolypeptide. The propeptide coding region may be obtained from the *Bacillus subtilis* alkaline protease gene (aprE), the *Bacillus subtilis* neutral protease gene (nprT), the *Saccharomyces cerevisiae* alpha-factor gene, the *Rhizomucor miehei* aspartic proteinase gene, or the *Myceliophthora thermophila* laccase gene (WO 95/33836).

Where both signal peptide and propeptide regions are present at the amino terminus of a polypeptide, the propeptide region is positioned next to the amino terminus of a polypeptide and the signal peptide region is positioned next to the amino terminus of the propeptide region.

It may also be desirable to add regulatory sequences which allow the regulation of the expression of the polypeptide relative to the growth of the host cell. Examples of regulatory systems are those which cause the expression of the gene to be turned on or off in response to a chemical or physical stimulus, including the presence of a regulatory compound. Regulatory systems in prokaryotic systems would include the lac, tac, and trp operator systems. In yeast, the ADH2 system or GAL1 system may be used. In filamentous fungi, the TAKA alpha-amylase promoter, *Aspergillus niger* glucoamylase promoter, and the *Aspergillus oryzae* glucoamylase promoter may be used as regulatory sequences. Other examples of regulatory sequences are those which allow for gene amplification. In eukaryotic systems, these include the dihydrofolate reductase gene which is amplified in the presence of methotrexate, and the metallothionein genes which are amplified with heavy metals. In these cases, the nucleic acid sequence encoding the polypeptide would be operably linked with the regulatory sequence.

Expression Vectors

The present invention also relates to recombinant expression vectors comprising a nucleic acid sequence of the present invention, a promoter, and transcriptional and translational stop signals. The various nucleic acid and control sequences described above may be joined together to produce a recombinant expression vector which may include one or more convenient restriction sites to allow for insertion or substitution of the nucleic acid sequence encoding the polypeptide at such sites. Alternatively, the polynucleotide of the present invention may be expressed by inserting the nucleic acid sequence or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus) which can be conveniently subjected to recombinant DNA procedures and can bring about the expression of the nucleic acid sequence. The choice of the vector will typically depend on the compatibility of the vector with the host cell into which the vector is to be introduced. The vectors may be linear or closed circular plasmids.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used.

The vectors of the present invention preferably contain one or more selectable markers which permit easy selection of transformed cells. A selectable marker is a gene the product of which provides for biocide or viral resistance, resistance to heavy metals, prototrophy to auxotrophs, and the like. Examples of bacterial selectable markers are the dal genes from *Bacillus subtilis* or *Bacillus licheniformis*, or markers which confer antibiotic resistance such as ampicillin, kanamycin, chloramphenicol or tetracycline resistance. Suitable markers for yeast host cells are ADE2, HIS3, LEU2, LYS2, MET3, TRP1, and URA3. A selectable marker for use in a filamentous fungal host cell may be selected from the group including, but not limited to, amdS (acetamidase), argB (ornithine carbamoyltransferase), bar (phosphinothricin acetyltransferase), hygB (hygromycin phosphotransferase), niaD (nitrate reductase), pyrG (orotidine-5'-phosphate decarboxylase), sC (sulfate adenyltransferase), trpC (anthranilate synthase), as well as equivalents from other species. Preferred for use in an *Aspergillus* cell are the amdS and pyrG genes of *Aspergillus nidulans* or *Aspergillus oryzae* and the bar gene of *Streptomyces hygroscopicus*.

The vectors of the present invention preferably contain an element(s) that permits stable integration of the vector into the host cell genome or autonomous replication of the vector in the cell independent of the genome of the cell.

For integration into the host cell genome, the vector may rely on the polynucleotide sequence encoding the polypeptide or any other element of the vector for stable integration of the vector into the genome by homologous or nonhomologous recombination. Alternatively, the vector may contain additional nucleic acid sequences for directing integration by homologous recombination into the genome of the host cell. The additional polynucleotide sequences enable the vector to be integrated into the host cell genome at a precise location(s) in the chromosome(s). To increase the likelihood of integration at a precise location, the integrational elements should preferably contain a sufficient number of nucleic acids, such as 100 to 1,500 base pairs, preferably 400 to 1,500 base pairs, and most preferably 800 to 1,500 base pairs, which are highly homologous with the corresponding target sequence to enhance the probability of homologous recombination. The integrational elements may be any sequence that is homologous with the target sequence in the genome of the host cell. Furthermore, the integrational elements may be non-encoding or encoding nucleic acid sequences. On the other hand, the vector may be integrated into the genome of the host cell by non-homologous recombination.

For autonomous replication, the vector may further comprise an origin of replication enabling the vector to replicate autonomously in the host cell in question. Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*. Examples of origins of replication for use in a yeast host cell are the 2 micron origin of replication, ARS1, ARS4, the combination of ARS1 and CEN3, and the combination of ARS4 and CEN6. The origin of replication may be one having a mutation which makes its functioning temperature-sensitive in the host cell (see, e.g., Ehrlich, 1978, *Proceedings of the National Academy of Sciences USA* 75: 1433).

More than one copy of a polynucleotide sequence of the present invention may be inserted into the host cell to increase production of the gene product. An increase in the copy number of the polynucleotide sequence can be obtained by integrating at least one additional copy of the sequence into the host cell genome or by including an amplifiable selectable marker gene with the nucleic acid sequence where cells containing amplified copies of the selectable marker gene, and thereby additional copies of the nucleic acid sequence, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a nucleic acid sequence of the invention, which are advantageously used in the recombinant production of the polypeptides. A vector comprising a nucleic acid sequence of the present invention is introduced into a host cell so that the vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be a unicellular microorganism, e.g., a prokaryote, or a non-unicellular microorganism, e.g., a eukaryote. Useful unicellular cells are bacterial cells such as gram positive bacteria including, but not limited to, a *Bacillus* cell, e.g., *Bacillus alkalophilus, Bacillus amyloliquefaciens, Bacillus brevis, Bacillus circulans, Bacillus clausii, Bacillus coagulans, Bacillus lautus, Bacillus lentus, Bacillus licheniformis, Bacillus megaterium, Bacillus stearothermophilus, Bacillus subtilis*, and *Bacillus thuringiensis*; or a *Streptomyces* cell, e.g., *Streptomyces lividans* or *Streptomyces murinus*, or gram negative bacteria such as *E. coli* and *Pseudomonas* sp. In a preferred embodiment, the bacterial host cell is a *Bacillus lentus, Bacillus licheniformis, Bacillus stearothermophilus* or *Bacillus subtilis* cell. In another preferred embodiment, the *Bacillus* cell is an alkalophilic *Bacillus*.

The introduction of a vector into a bacterial host cell may, for instance, be effected by protoplast transformation (see, e.g., Chang and Cohen, 1979, *Molecular General Genetics*

168: 111-115), using competent cells (see, e.g., Young and Spizizin, 1961, *Journal of Bacteriology* 81: 823-829, or Dubnau and Davidoff-Abelson, 1971, *Journal of Molecular Biology* 56: 209-221), electroporation (see, e.g., Shigekawa and Dower, 1988, *Biotechniques* 6: 742-751), or conjugation (see, e.g., Koehler and Thorne, 1987, *Journal of Bacteriology* 169: 5771-5278).

The host cell may be a eukaryote, such as a mammalian cell (e.g., human cell), an insect cell, a plant cell or a fungal cell. Mammalian host cells that could be used include but are not limited to human HeLa, 293, H9 and Jurkat cells, mouse NIH3T3 and C127 cells, Cos 1, Cos 7 and CV1, quail QC1-3 cells, mouse L cells and Chinese Hamster ovary (CHO) cells. These cells may be transfected with a vector containing a transcriptional regulatory sequence, a protein coding sequence and transcriptional termination sequences. Alternatively, the polypeptide can be expressed in stable cell lines containing the polynucleotide integrated into a chromosome. The co-transfection with a selectable marker such as dhfr, gpt, neomycin, hygromycin allows the identification and isolation of the transfected cells.

The host cell may be a fungal cell. "Fungi" as used herein includes the phyla Ascomycota, Basidiomycota, Chytridiomycota, and Zygomycota (as defined by Hawksworth et al., In, *Ainsworth and Bisby's Dictionary of The Fungi*, 8th edition, 1995, CAB International, University Press, Cambridge, UK) as well as the Oomycota (as cited in Hawksworth et al., 1995, supra, page 171) and all mitosporic fungi (Hawksworth et al., 1995, supra). The fungal host cell may also be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, F. A., Passmore, S. M., and Davenport, R. R., eds, *Soc. App. Bacteriol. Symposium Series No. 9*, 1980). The fungal host cell may also be a filamentous fungal cell. "Filamentous fungi" include all filamentous forms of the subdivision Eumycota and Oomycota (as defined by Hawksworth et al., 1995, supra). The filamentous fungi are characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

Fungal cells may be transformed by a process involving protoplast formation, transformation of the protoplasts, and regeneration of the cell wall in a manner known per se. Suitable procedures for transformation of *Aspergillus* host cells are described in EP 238 023 and Yelton et al., 1984, *Proceedings of the National Academy of Sciences USA* 81: 1470-1474. Suitable methods for transforming *Fusarium* species are described by Malardier et al., 1989, *Gene* 78: 147-156 and WO 96/00787. Yeast may be transformed using the procedures described by Becker and Guarente, In Abelson, J. N. and Simon, M. I., editors, *Guide to Yeast Genetics and Molecular Biology*, Methods in Enzymology, Volume 194, pp 182-187, Academic Press, Inc., New York; Ito et al., 1983, *Journal of Bacteriology* 153: 163; and Hinnen et al., 1978, *Proceedings of the National Academy of Sciences USA* 75: 1920.

Methods of Production

The present invention also relates to methods for producing a polypeptide of the present invention comprising (a) cultivating a host cell under conditions conducive for production of the polypeptide; and (b) recovering the polypeptide.

In the production methods of the present invention, the cells are cultivated in a nutrient medium suitable for production of the polypeptide using methods known in the art. For example, the cell may be cultivated by shake flask cultivation, small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptides may be detected using methods known in the art that are specific for the polypeptides. These detection methods may include use of specific antibodies, formation of an enzyme product, or disappearance of an enzyme substrate. In a specific embodiment, an enzyme assay may be used to determine the activity of the polypeptide. For example, human RhoC can be assayed by its ability to act as a guanosine triphosphatase.

The resulting polypeptide may be recovered by methods known in the art. For example, the polypeptide may be recovered from the nutrient medium by conventional procedures including, but not limited to, centrifugation, filtration, extraction, spray-drying, evaporation, or precipitation.

The polypeptides of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, J.-C. Janson and Lars Ryden, editors, VCH Publishers, New York, 1989).

Antibodies

According to the invention, the human RhoC polypeptide produced according to the method of the present invention may be used as an immunogen to generate any of these antibodies. Such antibodies include but are not limited to polyclonal, monoclonal, chimeric, single chain, Fab fragments, and a Fab expression library.

Various procedures known in the art may be used for the production of antibodies. For the production of antibody, various host animals can be immunized by injection with the polypeptide thereof, including but not limited to rabbits, mice, rats, sheep, goats, etc. In one embodiment, the polypeptide or fragment thereof can optionally be conjugated to an immunogenic carrier, e.g., bovine serum albumin (BSA) or keyhole limpet hemocyanin (KLH). Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *Corynebacterium parvum*.

For preparation of monoclonal antibodies directed toward the human RhoC polypeptide, any technique that provides for the production of antibody molecules by continuous cell lines in culture may be used. These include but are not limited to the hybridoma technique originally developed by Kohler and Milstein (1975, Nature 256:495-497), as well as the trioma technique, the human B-cell hybridoma technique (Kozbor et al., 1983, Immunology Today 4:72), and the EBV-hybridoma technique to produce human monoclonal antibodies (Cole et al., 1985, in Monoclonal Antibodies and Cancer Therapy, Alan R. Liss, Inc., pp. 77-96). In an additional embodiment of the invention, monoclonal antibodies can be produced in germ-free animals utilizing recent technology (PCT/US90/02545). According to the invention, human antibodies may be used and can be obtained by using human hybridomas (Cote et al., 1983, Proc. Natl. Acad. Sci. U.S.A. 80:2026-2030) or by transforming human B cells with EBV virus in vitro (Cole et al., 1985, in Monoclonal Antibodies and Cancer Therapy, Alan R. Liss, pp. 77-96). In fact, according to the invention, techniques developed for the production of "chimeric antibodies" (Morrison et al., 1984, J. Bacteriol. 159-870; Neuberger et al., 1984, Nature 312:604-608; Takeda et al., 1985, Nature 314:452-454) by splicing the genes from a mouse antibody molecule specific for the human RhoC polypeptide together with genes from a human antibody molecule of appropriate biological activity can be used; such antibodies are within the scope of this invention.

According to the invention, techniques described for the production of single chain antibodies (U.S. Pat. No. 4,946,778) can be adapted to produce polypeptide-specific single chain antibodies. An additional embodiment of the invention utilizes the techniques described for the construction of Fab expression libraries (Huse et al., 1989, Science 246:1275-1281) to allow rapid and easy identification of monoclonal Fab fragments with the desired specificity for the human RhoC polypeptide.

Antibody fragments which contain the idiotype of the antibody molecule can be generated by known techniques. For example, such fragments include but are not limited to: the F(ab')$_2$ fragment which can be produced by pepsin digestion of the antibody molecule; the Fab' fragments which can be generated by reducing the disulfide bridges of the F(ab')$_2$, fragment, and the Fab fragments which can be generated by treating the antibody molecule with papain and a reducing agent.

In the production of antibodies, screening for the desired antibody can be accomplished by techniques known in the art, e.g., radioimmunoassay, ELISA (enzyme-linked immunosorbent assay), "sandwich" immunoassays, immunoradiometric assays, gel diffusion precipitin reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention. For example, to select antibodies that recognize a specific epitope of a particular polypeptide, one may assay generated hybridomas for a product that binds to a particular polypeptide fragment containing such epitope. For selection of an antibody specific to a particular polypeptide from a particular species of animal, one can select on the basis of positive binding with the polypeptide expressed by or isolated from cells of that species of animal.

Immortal, antibody-producing cell lines can also be created by techniques other than fusion, such as direct transformation of B lymphocytes with oncogenic DNA, or transfection with Epstein-Barr virus. See, e.g., M. Schreier et al., "Hybridoma Techniques" (1980); Hammerling et al., "Monoclonal Antibodies And T-cell Hybridomas" (1981); Kennett et al., "Monoclonal Antibodies" (1980); see also U.S. Pat. Nos. 4,341,761; 4,399,121; 4,427,783; 4,444,887; 4,451,570; 4,466,917; 4,472,500; 4,491,632; 4,493,890.

Substrate

In a specific embodiment, the polynucleotides of the present invention, particularly, the polynucleotide fragments or antisense nucleic acids hybridizing to non-coding regions of SEQ ID NO:2 may be attached to a substrate. A substrate may be solid or porous, planar or non-planar, unitary or distributed. The polynucleotide may be attached covalently or applied to a derivatized surface in a chaotropic agent that facilitates denaturation and adherence by presumed non-covalent interactions, or some combinations thereof.

In a more specific embodiment, the substrate is a microarray. "Microarray" as defined herein is a substrate-bound collection of a plurality of nucleic acids, hybridization to each of the plurality of bound nucleic acids being separately detectable. The microarray may comprise a plurality of polynucleotides hybridizing to a non-coding region of SEQ ID NO:2. Alternatively the microarray may comprise a polynucleotide(s) hybridizing to said non-coding region and/or coding regions of SEQ ID NO:2.

Uses of Polynucleotides

Diagnostics

Polynucleotide fragments containing non-coding regions of SEQ ID NO:2 may be used as probes for detecting variants in genomic nucleotide samples from a patient. The variants may be allelic variants or substitution, insertion or deletion nucleotide variants. Genomic DNA may be isolated from the patient. A mutation(s) may be detected by Southern blot analysis, specifically by hybridizing restriction digested genomic DNA to various probes between 10-500 nucleotides in length, preferably between 20-200 nucleotides in length, more preferably between 20-100 nucleotides in length and most preferably between 20-60 nucleotides in length and subjecting to agarose electrophoresis. Alternatively, these polynucleotides may be used as PCR primers between about 10-100 nucleotides in length and be used to amplify the genomic DNA isolated from the patients. Methods for performing primer-directed amplification (routine or long range PCR) are well known in the art (see, for example, PCR Basics: From Background to Bench, Springer Verlag (2000); Gelfand et al., (eds), PCR Strategies, Academic Press (1998). Single base extension (see, for example, U.S. Pat. No. 6,004,744) may be used to detect SNPs.

These polynucleotide fragments may also be used to detect a sequence encoding RhoC in a sample. Specifically, the presence of a sequence encoding RhoC, variant or reverse complement thereof may be detected in a sample by contacting the sample with an oligonucleotide comprising at least 15, 16, 17, 18 or 19 nucleotides in length and may be between 15-5000 nucleotides in length and may preferably be between 20-60 nucleotides in length, that hybridizes to a non coding region of an RhoC gene. The non-coding region includes but is not limited to an intron, a splice junction, a 5'-non-coding region, an expression control sequence, a transcription factor binding site region and a 3'-non-coding region.

Additionally, primers may be obtained by routine or long range PCR that yield products containing contiguous intron/exon sequences and products containing more than one exon with intervening intron(s). The sequence of the amplified genomic DNA from the patient may be determined using methods known in the art. Such primers or probes may be between 15-5000 nucleotides in length and may preferably be between 20-60 nucleotides in length.

Thus the invention is thus directed to kits comprising these polynucleotide probes. In a specific embodiment, these probes are labeled with a detectable substance. Thus, these polynucleotides may be used to diagnose breast or pancreatic cancer or melanoma.

In one embodiment, the probes are in solution. In another embodiment, the probes are attached to a substrate. In a specific embodiment, the probes are contained within a microarray and are separately detectable.

Antisense Oligonucleotides and Mimetics

The antisense oligonucleotides or mimetics of the present invention may be used to decrease levels of a polypeptide. For example, over-expression of human RhoC has been found to be associated with the metastatic spread of melanomas and with the virulence of breast and pancreatic cancers. Therefore, the human RhoC antisense oligonucleotides of the present invention could be used to inhibit tumor growth and in particular, to treat metastatic melanomas.

The antisense oligonucleotides of the present invention may be formulated into pharmaceutical compositions. These compositions may be administered in a number of ways depending upon whether local or systemic treatment is desired and upon the area to be treated. Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

Compositions and formulations for oral administration include powders or granules, suspensions or solutions in water or non-aqueous media, capsules, sachets or tablets. Thickeners, flavoring agents, diluents, emulsifiers, dispersing aids or binders may be desirable.

Compositions and formulations for parenteral, intrathecal or intraventricular administration may include sterile aqueous solutions that may also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, liquid syrups, soft gels, suppositories, and enemas. The compositions of the present invention may also be formulated as suspensions in aqueous, non-aqueous or mixed media. Aqueous suspensions may further contain substances that increase the viscosity of the suspension including, for example, sodium carboxymethylcellulose, sorbitol and/or dextran. The suspension may also contain stabilizers.

In one embodiment of the present invention, the pharmaceutical compositions may be formulated and used as foams. Pharmaceutical foams include formulations such as, but not limited to, emulsions, microemulsions, creams, jellies and liposomes. While basically similar in nature these formulations vary in the components and the consistency of the final product. The preparation of such compositions and formulations is generally known to those skilled in the pharmaceutical and formulation arts and may be applied to the formulation of the compositions of the present invention.

The formulation of therapeutic compositions and their subsequent administration is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on $EC_{50}$ as found to be effective in in vitro and in vivo animal models.

In general, dosage is from 0.01 ug to 10 g per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligonucleotide is administered in maintenance doses, ranging from 0.01 ug to 10 g per kg of body weight, once or more daily, to once every 20 years.

Gene Therapy

As noted above, human RhoC is a member of Ras superfamily of GTPases that are critical elements in signal transduction pathways governing cell proliferation and cell death. Thus, the RhoC gene can be used in disorders of cell proliferation or apoptosis in which little or no RhoC is expressed. These include but are not limited to HIV, neurodegenerative or neuromuscular diseases, ischemic stroke, anoxia, ischemia/reperfusion damage and intoxication septic shock.

As described herein, the polynucleotide of the present invention may be introduced into a patient's cells for therapeutic uses. As will be discussed in further detail below, cells can be transfected using any appropriate means, including viral vectors, as shown by the example, chemical transfectants, or physico-mechanical methods such as electroporation and direct diffusion of DNA. See, for example, Wolff, Jon A, et al., "Direct gene transfer into mouse muscle in vivo,"

*Science,* 247, 1465-1468, 1990; and Wolff, Jon A, "Human dystrophin expression in mdx mice after intramuscular injection of DNA constructs," *Nature,* 352, 815-818, 1991. As used herein, vectors are agents that transport the gene into the cell without degradation and include a promoter yielding expression of the gene in the cells into which it is delivered. As will be discussed in further detail below, promoters can be general promoters, yielding expression in a variety of mammalian cells, or cell specific, or even nuclear versus cytoplasmic specific. These are known to those skilled in the art and can be constructed using standard molecular biology protocols. Vectors have been divided into two classes:

a) Biological agents derived from viral, bacterial or other sources.

b) Chemical physical methods that increase the potential for gene uptake, directly introduce the gene into the nucleus or target the gene to a cell receptor.

Biological Vectors

Viral vectors have higher transaction (ability to introduce genes) abilities than do most chemical or physical methods to introduce genes into cells. Vectors that may be used in the present invention include viruses, such as adenoviruses, adeno associated virus (AAV), vaccinia, herpesviruses, baculoviruses and retroviruses, bacteriophages, cosmids, plasmids, fungal vectors and other recombination vehicles typically used in the art which have been described for expression in a variety of eukaryotic and prokaryotic hosts, and may be used for gene therapy as well as for simple protein expression. Polynucleotides are inserted into vector genomes using methods well known in the art.

Retroviral vectors are the vectors most commonly used in clinical trials, since they carry a larger genetic payload than other viral vectors. However, they are not useful in non-proliferating cells. Adenovirus vectors are relatively stable and easy to work with, have high titers, and can be delivered in aerosol formulation. Pox viral vectors are large and have several sites for inserting genes, they are thermostable and can be stored at room temperature.

Examples of promoters are SP6, T4, T7, SV40 early promoter, cytomegalovirus (CMV) promoter, mouse mammary tumor virus (MMTV) steroid-inducible promoter, Moloney murine leukemia virus (MMLV) promoter, phosphoglycerate kinase (PGK) promoter, and the like. Alternatively, the promoter may be an endogenous adenovirus promoter, for example the E1 a promoter or the Ad2 major late promoter (MLP). Similarly, those of ordinary skill in the art can construct adenoviral vectors utilizing endogenous or heterologous poly A addition signals.

Plasmids are not integrated into the genome and the vast majority of them are present only from a few weeks to several months, so they are typically very safe. However, they have lower expression levels than retroviruses and since cells have the ability to identify and eventually shut down foreign gene expression, the continuous release of DNA from the polymer to the target cells substantially increases the duration of functional expression while maintaining the benefit of the safety associated with non-viral transfections.

Chemical/Physical Vectors

Other methods to directly introduce genes into cells or exploit receptors on the surface of cells include the use of liposomes and lipids, ligands for specific cell surface receptors, cell receptors, and calcium phosphate and other chemical mediators, microinjections directly to single cells, electroporation and homologous recombination. Liposomes are commercially available from Gibco BRL, for example, as LIPOFECTIN® and LIPOFECTACE®, which are formed of cationic lipids such as N-[1-(2,3 dioleyloxy)-propyl]-n,n,n-trimethylammonium chloride (DOTMA) and dimethyl dioctadecylammonium bromide (DDAB). Numerous methods are also published for making liposomes, known to those skilled in the art.

For example, Nucleic acid-Lipid Complexes—Lipid carriers can be associated with naked nucleic acids (e.g., plasmid DNA) to facilitate passage through cellular membranes. Cationic, anionic, or neutral lipids can be used for this purpose. However, cationic lipids are preferred because they have been shown to associate better with DNA that, generally, has a negative charge. Cationic lipids have also been shown to mediate intracellular delivery of plasmid DNA (Feigner and Ringold, Nature 337:387 (1989)). Intravenous injection of cationic lipid-plasmid complexes into mice has been shown to result in expression of the DNA in lung (Brigham et al., Am. J. Med. Sci. 298:278 (1989)). See also, Osaka et al., J. Pharm. Sci. 85(6):612-618 (1996); San et al., Human Gene Therapy 4:781-788 (1993); Senior et al., Biochemica et Biophysica Acta 1070:173-179 (1991); Kabanov and Kabanov, Bioconjugate Chem. 6:7-20 (1995); Remy et al., Bioconjugate Chem. 5:647-654 (1994); Behr, J-P., Bioconjugate Chem 5:382-389 (1994); Behr et al., Proc. Natl. Acad. Sci., USA 86:6982-6986 (1989); and Wyman et al., Biochem. 36:3008-3017 (1997).

Cationic lipids are known to those of ordinary skill in the art. Representative cationic lipids include those disclosed, for example, in U.S. Pat. No. 5,283,185; and e.g., U.S. Pat. No. 5,767,099. In a preferred embodiment, the cationic lipid is N.sup.4-spermine cholesteryl carbamate (GL-67) disclosed in U.S. Pat. No. 5,767,099. Additional preferred lipids include N4_spermidine cholestryl carbamate (GL-53) and 1-(N-4-spermind)-2,3-dilaurylglycerol carbamate (GL-89).

The vectors of the invention may be targeted to specific cells by linking a targeting molecule to the vector. A targeting molecule is any agent that is specific for a cell or tissue type of interest, including for example, a ligand, antibody, sugar, receptor, or other binding molecule.

Invention vectors may be delivered to the target cells in a suitable composition, either alone, or complexed, as provided above, comprising the vector and a suitably acceptable carrier. The vector may be delivered to target cells by methods known in the art, for example, intravenous, intramuscular, intranasal, subcutaneous, intubation, lavage, and the like. The vectors may be delivered via in vivo or ex vivo applications. In vivo applications involve the direct administration of an adenoviral vector of the invention formulated into a composition to the cells of an individual. Ex vivo applications involve the transfer of the adenoviral vector directly to harvested autologous cells which are maintained in vitro, followed by readministration of the transduced cells to a recipient.

In a specific embodiment, the vector is transfected into antigen-presenting cells. Suitable sources of antigen-presenting cells (APCs) include, but are not limited to, whole cells such as dendritic cells or macrophages; purified MHC class 1 molecule complexed to beta2-microglobulin and foster antigen-presenting cells. In a specific embodiment, the vectors of the present invention may be introduced into T cells or B cells using methods known in the art (see, for example, Tsokos and Nepom, 2000, J. Clin. Invest. 106:181-183).

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

Various references are cited herein, the disclosure of which are incorporated by reference in their entireties.

What is claimed is:

1. An isolated genomic nucleic acid molecule, said nucleic acid molecule obtainable from human chromosome 1, selected from the group consisting of:
   a) an isolated polynucleotide consisting of a nucleic acid sequence which is at least 99% identical to the full length polynucleotide of SEQ ID NO:2, which encodes a polypeptide which is at least 99% identical to the amino acid sequence of SEQ ID NO: 1,
   b) an isolated polynucleotide fragment of (a) which comprises at least nucleotides 3959-6218 of SEQ ID NO:2, which encodes a polypeptide which is at least 99% identical to the amino acid sequence of SEQ ID NO: 1, and
   c) a full complement of (a) or (b).

2. A nucleic acid construct comprising an isolated genomic nucleic acid molecule, said nucleic acid molecule obtainable from human chromosome 1, selected from the group consisting of:
   a) an isolated polynucleotide consisting of a nucleic acid sequence which is at least 99% identical to the full length polynucleotide of SEQ ID NO:2, which encodes a polypeptide which is at least 99% identical to the amino acid sequence of SEQ ID NO: 1,
   b) an isolated polynucleotide fragment of (a) which comprises at least nucleotides 3959-6218 of SEQ ID NO:2, which encodes a polypeptide which is at least 99% identical to the amino acid sequence of SEQ ID NO: 1, and
   c) a full complement of (a) or (b).

3. An expression vector comprising an isolated genomic nucleic acid molecule, said nucleic acid molecule obtainable from human chromosome 1, selected from the group consisting of:
   a) an isolated polynucleotide consisting of a nucleic acid sequence which is at least 99% identical to the full length polynucleotide of SEQ ID NO:2, which encodes a polypeptide which is at least 99% identical to the amino acid sequence of SEQ ID NO: 1,
   b) an isolated polynucleotide fragment of (a) which comprises at least nucleotides 3959-6218 of SEQ ID NO:2, which encodes a polypeptide which is at least 99% identical to the amino acid sequence of SEQ ID NO: 1, and
   c) a full complement of (a) or (b).

4. A recombinant host cell comprising an isolated genomic nucleic acid molecule, said nucleic acid molecule obtainable from human chromosome 1, selected from the group consisting of:
   a) an isolated polynucleotide consisting of a nucleic acid sequence which is at least 99% identical to the full length polynucleotide of SEQ ID NO:2, which encodes a polypeptide which is at least 99% identical to the amino acid sequence of SEQ ID NO: 1, b) an isolated polynucleotide fragment of (a) which comprises at least nucleotides 3959-6218 of SEQ ID NO:2, which encodes a polypeptide which is at least 99% identical to the amino acid sequence of SEQ ID NO: 1, and c) a full complement of (a) or (b).

5. A method for obtaining a polypeptide encoded by a nucleic acid molecule obtainable from human chromosome 1, said polypeptide consisting of human RhoC or a variant thereof comprising:
   (a) culturing the recombinant host cell of claim 4 under conditions that provide for the expression of said polypeptide and
   (b) recovering said expressed polypeptide.

6. A composition comprising the nucleic acid molecule of claim 1 and a pharmaceutically acceptable carrier.

7. A method for detecting the presence of the nucleic acid molecule of claim 1 in a sample, comprising contacting the sample with a polynucleotide probe comprising at least 20 contiguous nucleotides that hybridizes to said nucleic acid molecule under stringent conditions and determining whether the polynucleotide probe binds to said nucleic acid molecule in the sample.

8. The nucleic acid molecule of claim 1, wherein said sequence encodes Rho C protein depicted in SEQ ID NO:1.

9. A kit comprising the nucleic acid molecule of claim 1.

10. A solid support comprising the nucleic acid molecule of claim 1.

11. The solid support of claim 10, wherein said solid support is a microarray.

* * * * *